(12) United States Patent
Van der Zel

(10) Patent No.: US 7,086,863 B2
(45) Date of Patent: Aug. 8, 2006

(54) METHOD FOR PRODUCTION OF AN ARTIFICIAL TOOTH

(75) Inventor: Joseph Maria Van der Zel, Hoorn (NL)

(73) Assignee: Cicero Dental Systems, B.V., Hoorn (NL)

( * ) Notice: Subject to any disclaimer, the term of this patent is extended or adjusted under 35 U.S.C. 154(b) by 343 days.

(21) Appl. No.: 10/312,148

(22) PCT Filed: Apr. 19, 2002

(86) PCT No.: PCT/NL02/00258

§ 371 (c)(1),
(2), (4) Date: Apr. 25, 2003

(87) PCT Pub. No.: WO02/085241

PCT Pub. Date: Oct. 31, 2002

(65) Prior Publication Data

US 2003/0207235 A1 Nov. 6, 2003

(30) Foreign Application Priority Data

Apr. 23, 2001 (EP) ................. 01201472

(51) Int. Cl.
*A61C 5/10* (2006.01)
*A61C 13/08* (2006.01)

(52) U.S. Cl. .................. 433/223; 264/19; 264/20

(58) Field of Classification Search .......... 433/223, 433/202.1; 264/19–20
See application file for complete search history.

(56) References Cited

U.S. PATENT DOCUMENTS

| 4,611,288 A * | 9/1986 | Duret et al. ............. 700/163 |
|---|---|---|
| 5,151,044 A * | 9/1992 | Rotsaert .................. 433/229 |
| 5,759,030 A | 6/1998 | Jung et al. |
| 5,766,006 A | 6/1998 | Murljacic |
| 5,800,164 A | 9/1998 | Pfau |
| 5,989,031 A | 11/1999 | Kura et al. |
| 6,174,168 B1 | 1/2001 | Dehoff et al. |
| 6,322,728 B1 * | 11/2001 | Brodkin et al. ............... 264/19 |
| 6,568,936 B1 * | 5/2003 | MacDougald et al. ...... 433/223 |
| 2001/0034010 A1 * | 10/2001 | MacDougald et al. ...... 433/223 |

(Continued)

FOREIGN PATENT DOCUMENTS

DE 199 44 130 A1 12/2001

(Continued)

*Primary Examiner*—John J Wilson
(74) *Attorney, Agent, or Firm*—The Webb Law Firm

(57) ABSTRACT

The invention relates to a method for producing an artificial tooth, comprising a base layer substantially determining strength and at least one cover layer substantially determining appearance of a finished artificial tooth, said method comprising: establishing the available outer shape and dimensions for the finished artificial tooth, e.g. with a CAD-CAM system; acquiring an image of a natural tooth to be replaced by the artificial tooth or a corresponding natural tooth over at least the in use visible outer surface thereof, including variations in appearance in said outer surface; determining in the appearance determining properties of the cover layer to correspond with the variations in the appearance of the natural tooth to be replaced or the corresponding natural tooth, and determining a thickness of the cover layer locally required for said correspondence; constructing the base layer to a shape and dimensions, which are based on the shape and dimensions available for the artificial tooth and prior to construction deducting, in the CAD-CAM system therefrom the locally required thickness of the cover layer; and applying the cover layer over the base layer to attain the available outer shape and dimensions for the finished artificial tooth.

20 Claims, 2 Drawing Sheets

U.S. PATENT DOCUMENTS

2002/0110786 A1 * 8/2002 Dillier .................. 433/213

FOREIGN PATENT DOCUMENTS

| EP | 0 796 596 B1 | 1/1998 |
| EP | 1 025 829 A1 | 8/2000 |
| FR | 2 669 526 A1 | 5/1992 |
| WO | WO 97/01308 A1 | 1/1997 |

* cited by examiner

METHOD FOR PRODUCTION OF AN ARTIFICIAL TOOTH

BACKGROUND OF THE INVENTION

1. Field of the Invention

The present invention relates to a method for producing an artificial tooth, being a reproduction of the original natural tooth to be replaced or a corresponding natural tooth. It is understandably desirable that the artificial tooth to be produced as a reproduction of an original natural element should be as natural a copy as possible. The natural appearance of the original natural element or tooth should be copied therefore as closely as possible. The appearance of both the artificial tooth and the original natural element is composed from a number of properties, such as color, translucency, lightness of the colors, brightness, etc.

2. Brief Description of the Related Art

In the field of the dental profession it has longsince been established, that the more natural reproductions—artificial teeth—can be produced from ceramic materials and/or acrylic materials. With these materials especially the translucency and/or transparency of the enamel of the original natural teeth can be well approximated.

The task of replacing a tooth is conventionally made of two separate steps. The first step is to measure the shape and color shade of a tooth to be replaced and the second step is to make a duplicate of that tooth according tot he measurements taken in the first step. In the first step, while the shape information can be acquired with molding technique, the measurement of the color shade and translucency of the tooth proves to be more challenging. The quality of the dental prosthesis cannot be better than the data that serves to model the original tooth. The precision of that model depends on several factors, like the quality of the illumination, the data acquisition by measuring and the processing of those data. The oldest and simplest way of determining the color shade of an object like a tooth is to compare visually the object with a chart of color shades. The results obtained with that method are however not very good because of the subjectivity of the human eye.

Furthermore, the illumination of the tooth and of the chart may cause inappropriate color shade choices. A quantitative method can be used to obtain a minimum of precision and of reproductability in the measurement of the color shade of an object. Such quantitative methods can be classified by the type of illumination used, the measurement technique, the data processing and the comparison between the finished product and the original object.

Another measurement technique is taught by Murljacic in his U.S. Pat. No. 5,766,006 issued on Jun. 16, 1998. In this document, Murljacic describes a tooth shade analyzer system using a camera to capture a digital color image of a tooth. The tooth image includes an RGB chromaticity representation that is scanned and compared pixel by pixel with several tooth shades stored in a memory of the system.

A drawback of Murljacic's system is that the scanning is performed without controlling the illumination therefore decreasing the reproductability of the color comparison. Several methods are known and used to convert the spectral decomposition or the data collected from a selected area into a single measurement that corresponds to the color perception of the human eye. The objective is to quantize the data and also to correct them as to be able to recreate the proper colors of the original model as the human eye perceives them. It is also important to be able to quantize the translucency of the materials.

In PCT WO. 97/01308 an oral camera connected to a shade analyzer subsystem, e.g. a digital video processor, and a color display monitor. The camera captures a digital color image of the patient's tooth and the subsystem compares that image to a stored plurality of tooth shades. Each tooth shade is represented in a block of data, including color image data, a toothshade digital word, and a manufacturer type. The patient's tooth image includes an RBG chromatically representation that is scanned and compared with the several tooth shades stored in memory, and a match is determined and communicated to a user of the system. The methodology includes the specification of fractional tooth shades, if needed, corresponding to a plurality of porcelain firms for manufacturing a reconstructed tooth.

The information is then used by a technician to layer the crown following the identified color shade as measured and presented by the digital device. This process of fabricating a crown by a way of layering the material by hand is fairly tedious and costly as it takes much hands-on time. The result of this hand-work is unpredictable especially the shape and dimensions and the result depends in a great deal on the skills of the dental technician.

In EP-0796596 a system for recording the form and shade structure of teeth is described. The system is applied in the preparation and the production of ceramic or acrylic veneered restorations. The system consists of different assortments containing the models and images as well as layering schemes of different tooth form and shade structures. At the patient a comparison is made between the form and shade of the patients' teeth with the models, whereby the best fitting assortment is selected and in the dental laboratory according to the accompanying layering schemes nature-like restorations can be reproduced.

Although the use of a computer is mentioned as an optional component of the assortment, all 2D-representations are directed to production of restorations in the dental laboratory. Because the restorations are layered without a volumetric control especially form, shape and dimensions of the finished artificial tooth of a computer aided manufacturing system subjective uncertainty remains in the final restoration.

In U.S. Pat. No. 5,759,030 a color measuring system and method such as for determining the color or other characteristics of teeth are described. Perimeter receiver fiber optics are spaced apart from a central source fiber optic and receive light reflected from the surface of the tooth being measured. The system utilizes the perimeter receiver fiber optics to determine information regarding the height and angle of the probe with respect to the tooth being measured. Under processor control, color measurement may be made at a predetermined height and angle. Translucency, fluorescence and/or surface texture data also may be obtained. The data generated by the system may be used to implement an automated material mixing machine for the material of which the prosthesis is made. Color and other data taken from a measurement may be used to determine or predict quantities of pigment or other materials for the recipe. Dental prostheses may be layered to simulate the degree of translucency of the tooth.

It is possible to measure for example four measurements for four regions of the tooth and send to the computer, with the data for the four color measurements (such as RBG or other values) associated with the four regions in accordance to the entered parameters.

Another advanced computer assisted system has become known as the Shade Scan System (Cortex Machina, Montreal, Quebec, Canada). It consists of an intraoral camera probe with specially designed optics that allows a spectral measurement of color and translucency. Instead of one or more local measurements on the tooth, as is done with the previous systems, the Shade Scan System includes a complete and global representation of the tooth's properties. The software consists of a shade selection process that translates the optical data into a simple and precise schematic color fields over the whole tooth. The color fields are identified and represented by numbers from an assortment of porcelain of a particular brand. The color fields can be selected as a fine discriminating sensitivity or a more coarser division of color fields. The software allows a representation of translucent areas with a dark-light shade mapping of the whole tooth. This makes the vertical height of the optically more dense areas of the tooth ("mamelons") visible.

Because results of the digital color analyzer only result in prosthesis through the manual labor of the dental technician, the pseudo trial and error methods are used in the manufacturing of the prosthesis remain, with the result that prosthesis needs to be remade, leading to increased costs and inconvenience to the patient, dental professional and dental laboratory.

SUMMARY OF THE INVENTION

It is an object of the present invention to provide an improved method for producing an artificial tooth as a reproduction of a natural tooth to be replaced by the restoration or a corresponding tooth.

It is accordingly an object of this invention to make the results of a digital shade analyzer available in a digital format in such a way that it can be used to model a crown layer build-up in a computer aided design system.

Still another object of the invention is to use the model of a layered crown build-up designed by computer, to subsequently use the model for fabrication of the crown in layers by a computer aided manufacturing system.

An object of the present invention is to reproduce a tooth in layers using a digital map of the natural element, design a layered internal build-up and automatically produce a layered tooth by subsequent production steps.

These and other objects of the invention will become apparent in the description which follows.

According to the present invention a method for production of an artificial tooth is provided. The method provided by the invention enables a fully automated production with little material loss and optimal results, in relation to both the shape, dimensions and form, as well as the appearance of the produced artificial tooth.

In addition, according to a preferred embodiment, the method can comprise the features of claim 2. Since especially ceramic material and acrylic materials exhibit a certain depth of looking. Thus the appearance of an additional cover layer can be influenced by an underlying first cover layer, which can then be arranged on the base layer. In this manner the combined optical properties of the layers is used to determine the local appearance of the finished artificial tooth.

By varying the thicknesses of the cover layer and an additional cover layer over the outer surface of the artificial tooth to be produced, as described in claim 3, variations over the surface of the artificial tooth to be produced in the optical appearance thereof can be achieved. This of course also holds true for an artificial tooth with a single cover layer, of which the thickness can be varied over the outer surface of the artificial tooth to be produced in order to vary the optical appearance thereof. Additionally the material properties of a single cover layer, as well as of the additional cover layer can be varied in order to achieve a desired variation in the appearance of the artificial tooth to be produced. Such physical material properties being changed could include adding an additive.

For the present invention the manner of applying layers can be: forming the base layer and/or the cover layer or layers with at least one process from the group of processes, comprising: 3D ink jet printing using STL files; Robocasting of material, e.g. in gel form; stereolithography (SLA); fused deposition (FD); laminated object manufacturing, etc.

It is noted here, that the present invention entails a novel and inventive approach to producing artificial teeth, where the final shape and dimensions of the tooth to be produced is determinative as a starting point. From this information and toward the inner regions of the artificial tooth to be produced in order to achieve the desired optical appearance thereof with the at least one cover layer. A computer aided manufacturing system involved uses the shape and dimensions of the artificial tooth to be produced and deducts therefrom the locally required thickness of the cover layer and/or cover layers, which are needed to obtain the desired optical appearance.

This is therefore a design method, which functions from the outside toward the inside of the artificial tooth to be produced, where the application or designed addition of each or any cover layer results in a decrease in the base layer thickness to accommodate said cover layers within the confines determined by the available shape and dimensions of the artificial tooth to be produced.

BRIEF DESCRIPTION OF THE DRAWINGS

The invention will be described further below, as well as advantages, features and alternatives within the scope of the claims, under reference to the accompanying drawings, wherein:

DETAILED DESCRIPTION OF THE PREFERRED EMBODIMENTS

Figure 1:
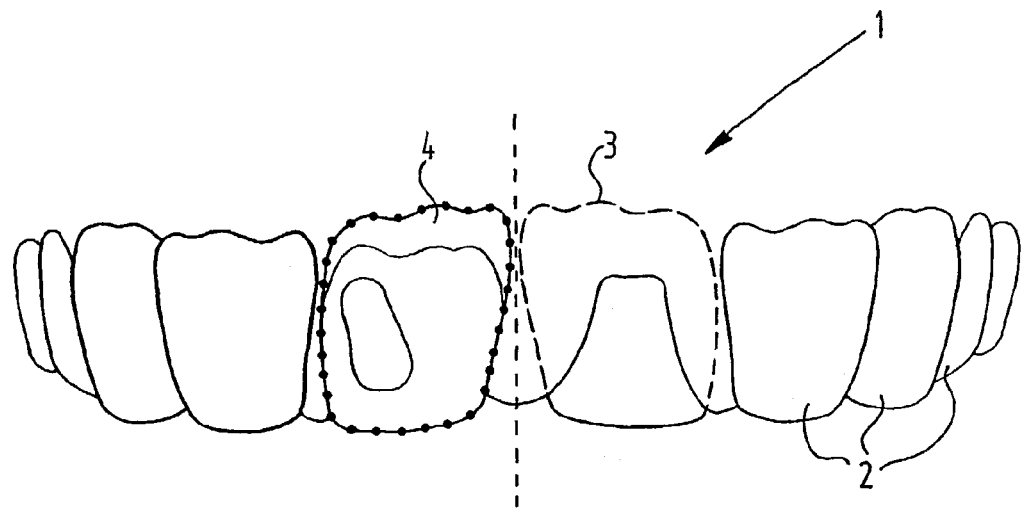
FIG. 1 is a schematic view of a natural array of teeth in the mouth of a patient, in which array a tooth needs to be replaced.

FIG. 1 shows an array 1 of teeth 2. One of the teeth needs to be replaced by an artificial tooth, of which the outline 3 is shown. The outline 3 of the artificial tooth to replace the original natural tooth, is a mirror image of the neighboring tooth 4. The outline 3 for the dental restoration or artificial tooth, to be produced according to the present invention is here taken as a mirror image of the adjoining or neighboring tooth 4, since the original natural tooth, which is to be replaced by the dental restoration, is not available for imaging. This can be the case, because parts of this original natural tooth may have broken off, or the like.

If the original natural tooth is still completely available, the shape now indicated by the outline 3 need not be taken from a neighboring or adjoining tooth 4, but can be taken from the original natural tooth. The outline 3 can be determined by an apparatus, which is conventional in itself, for imaging the dental restoration to be produced, for instance based on a CAD-CAM system.

Apart from the outline 3, the complete shape and dimensions of the dental restoration to be produced according to the present invention are determined. Furthermore, also a color analysis of the neighboring tooth 4 is executed. Based on the color analysis four distinct color feature regions 5, 6 and 7 are identified, whereas a fourth region 8, which is known as the mamelon region appears to be buried within the inside of the tooth. The two cross sections II—II and IV—IV in FIGS. 2 and 4 resp. show the manner, in which the artificial tooth is constructed in according with the present invention in order to achieve the desired appearance properties.

According to the method of the present invention the outer shape and dimensions and outline of the artificial tooth to be produced are taken as a given. In designing the artificial tooth to be produced at least one cover layer is arranged within the limitation of the outline, shape and dimensions of the artificial tooth to be produced. In applying this design method a base layer, which essentially determines the strength of the artificial tooth to be produced, and which is designated with reference number 9, is reduced further for each cover layer arranged within the limitations of the final shape and dimensions of the tooth to be produced. The base layer 9 is, as it were, the carrier for the cover layers.

Figures 2, 3, 4:
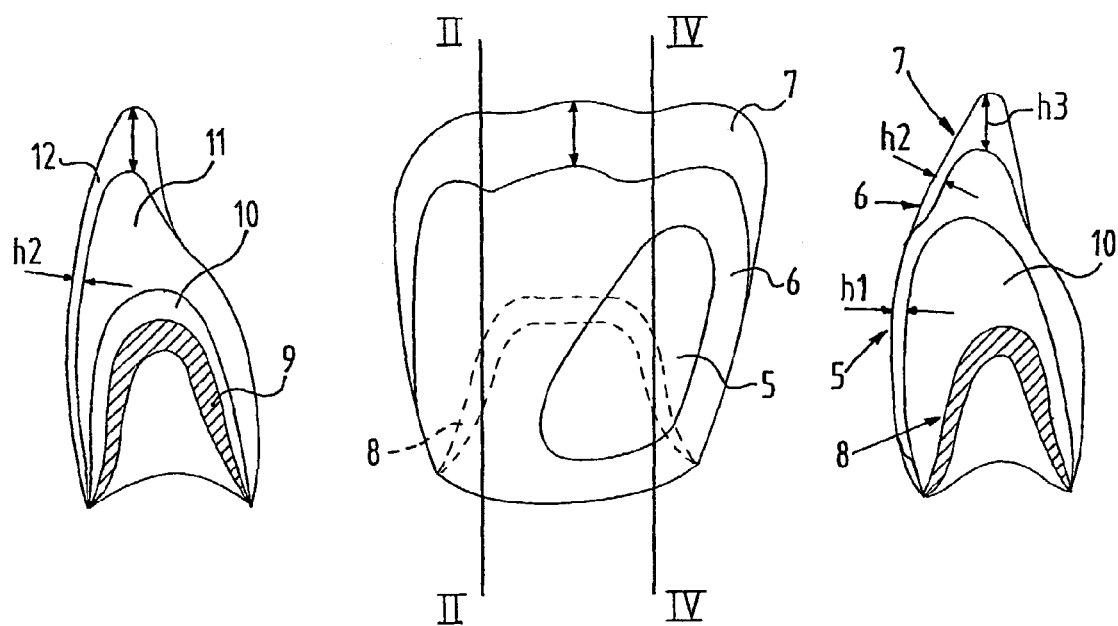
FIGS. 2, 3 and 4 are sectional views showing the appearance and two cross sectional views of an artificial tooth, produced in accordance with the present invention.

From FIGS. 2, 3 and 4 it is apparent, that the base layer 9 is not only determinative for the strength of the artificial tooth to be produced, but is also used to emulate the mamelon structure 8. On the base layer 9 a first cover layer 10 is arranged, which is most determinative for the color region 5 on the outside of the artificial tooth, which is apparent from a comparison of FIGS. 2 and 4 in combination with FIG. 3. Region 5 is for instance whiter and more bright than regions 6 and 7, where region 7 is again more bright, but less opaque than region 6, but less bright than region 5.

Region 6 is obtained from a combination of cover layers 11 and 12, of which 12 has, at least in approximation, a specific thickness, so that the cover layer 11 has a desired effect on the appearance of the artificial tooth through the cover layer 12.

Further, region 7 is evidently obtained primarily by cover layer 12.

Again it is noted here, that the configuration is designed, for example using a CAD-CAM system, starting from the outer shape and dimensions of the artificial tooth to be produced and inserting within these shape and dimensions cover layers, thereby reducing in the design, prior to actual production, the base layer locally, where required to obtain the desired appearance with the cover layers 10, 11, 12 in isolation, in combination with each other, or in combination with the base layer 9.

Figure 6:
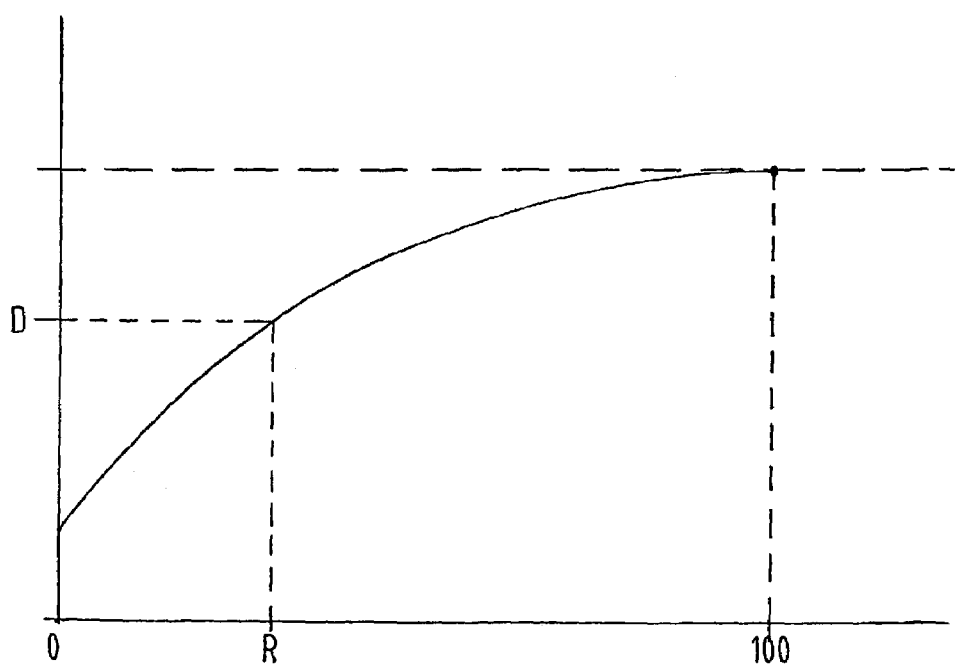
FIG. 6 is a graph showing the effect of the ratio in thicknesses of two cover layers.

FIG. 6 shows the effect of combining cover layers having specific thicknesses upon a specific appearance characteristics, such as color, translucence, etc. The appearance characteristic is arranged along the vertical axis, whereas the ratio between thicknesses of subsequent cover layers is set out along the horizontal axis. It is apparent, that in the origin of the graph there is only one cover layer and the optical characteristics, such as color, translucence, etc. is determined entirely by the other cover layer. As the second or additional cover layer is added and the ratio between the thicknesses of the two cover layers increases in the favor of the added cover layer, the influence of the original cover layer on the appearance characteristics diminishes. When only the additional cover layer remains or has such a thickness, that the looking depth thereinto is no longer sufficient for the underlying cover layer to have any effect (this is designated with "100" along the horizontal axis in FIG. 6), the appearance characteristics is entirely determined by the additional cover layer.

Every combination of materials for the cover layer and the additional cover layer has a specific graph. Having knowledge of these graphs a desired appearance characteristic, (which in FIG. 6 is designated with "D" along the vertical axis) can be achieved by applying the corresponding ratio "R" between the thicknesses of the original cover layer and the original cover layer, which ratio "R" is shown along the horizontal axis in FIG. 6.

Figure 5:
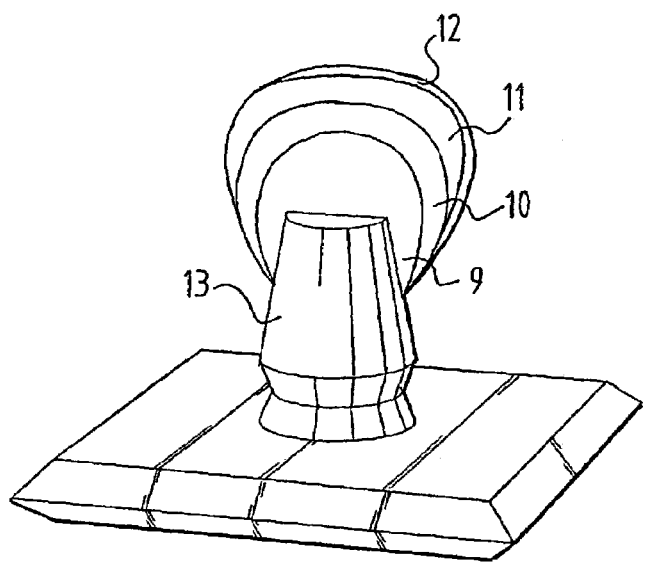
FIG. 5 is a perspective view of a configuration of an artificial tooth to be produced according to the present invention in cross section.

In FIG. 5 a possible production technique is shown. The design of the artificial tooth to be produced has here been completed beforehand and is based, as is described hereinabove, upon a approach from the outside toward the inside of the artificial tooth to be produced. With the completed design in hand a computer aided manufacturing process can be employed to apply on a stand 13 consecutive base layer 9, and cover layers 10, 11 and 12 having the desired local thicknesses. Local thicknesses is an expression used to indicate the thickness in a direction, in which the artificial tooth will be viewed from outside, when arranged in a patient's mouth.

The production technique for a layered artificial tooth or crown is in itself known and is for example described in U.S. Pat. No. 4,937,928 having the title "method of making a dental crown for a dental preparation by means of a CAD-CAM system", which is incorporated by reference herein entirely.

A simple linear regression analyses for lightness (L*), redness (a*), yellowness (b*) and translucency parameters (TP) was performed on a series of composite combinations is used to divide the surface in defined areas when seen in a 2D front view.

Natural teeth show a gradual increase in lightness from incisal to center sites of the tooth. The lightness decreases slightly toward the cervical site. Both redness and yellowness of natural teeth tend to increase in the direction of the cervical site, being affected by gingival pink for redness, root color, and a thin layer of enamel for yellowness, respectively, along the tooth axis toward the cervical site. TP tends to decrease toward the cervical site.

It is quire difficult to measure the translucency of a natural tooth by spectroradiometric color computer, which is a noncontact instrument. An objective and universal method has been to evaluate the translucency of the natural tooth or shade guide by measuring the reflection spectra under white and black backings by means of a digital spectra Colorimeter device. The measurement of TP, according to this invention, has shown to be a proper and simple way to evaluate the translucency of in vivo natural teeth.

The method of taking a color and translucency measurement consists in performing the following steps in sequence.
1. Starting the apparatus
2. Illuminating the tooth via a predetermined illumination method
3. Calibrating the CCD camera
4. Acquiring data pertaining to the color shade and translucency of the tooth
5. Optionally, verifying that the initial calibration is correct; if not (step 6) returning to step 2
6. Processing the data to produce a color shade image map and a translucency image map 7. Optionally, after a duplicate tooth has been made from the data of the color shade and translucency image maps, the image of the duplicate tooth may be acquired by placing the duplicate tooth in place of the original tooth and by performing steps 1 to 5 to yield duplicate color shade image and translucency image maps that may be compared to the original maps to control the quality of the finished product; and
8. Stopping the apparatus.

These general steps will now be further described.

Illumination

The purpose of the illumination in step two is to illuminate the object to measure, i.e., the tooth 4 (FIG. 1). As will be further described hereinbelow, the data acquisition step requires that the illumination is known with a precision of at least one percent everywhere on the tooth surface. A telecentric configuration, meets the specifications for dental applications. A light source projecting light rays should be powerful enough to drown other ambient light sources to thereby ensure that the characteristics of the illumination of the tooth are known.

Calibration

Measurement of the color and translucency of a tooth depends critically on the illumination and sensor characteristics at the time the measurement is made. The third step is the calibration of these factors by taking measurements of a first calibration target consisting of a collection of patches of known color shades, translucencies, and other appearance factors. From these measurements a mathematical transform that will convert the measured values into standard ones.

After the calibration step, the tooth to be duplicated can be measured (step four). This measurement step may also be called the data acquisition step. The objective of the measurement step five is to acquire data to build a color shade image map and a translucency image map in the data-processing step six.

Data Acquisition

Color Analysis

The color analysis consists in doing a tristimulus calculation. Such a calculation of the so called X, Y and Z tristimulus values are believed well known in the art and will not be described herein. The human perception of color is limited by the fact that the retina samples light through three spectral bands, the tristimulus values. These and the CIE LAB colors are normally computed from full spectra using CIE (Commission Internationale de I'Eclairage) prescribed methods. Resulting from these measurements values for lightness L*, redness a* and yellowness b* can be calculated. A linear transform is used to compute the tristimulus values from only three samples of the spectra. The CIE color of teeth can be accurately measured using the three sampling bands provided by the red, green and blue channels of the CCD camera. It has been found that under certain mathematical criteria, relating to the range of spectra to be measured, the spectra of the L, a and b tristimulus computations, and the spectra of the sampling bands, it is possible to compute the tristimulus values directly from the sampling band values using a linear transform.

For example, giving $x=(L,a,b)^T$, a vector of tristimulus values computed from the reflectance spectra of some object, and $r=(r, g, b)^T$ is a vector of red, green and blue values as measured by the CCD camera under exactly the same illumination conditions, then there are circumstances in which the two quantities will be related by some non-linear vector function. The parameters of the linear transform are derived during the calibration from the known CIE LAB colors of the appearance patches described hereinabove. With the method described hereinabove, it is possible to measure CIE LAB color at every pixel of the CCD camera image both because the computation is fast and because the linear transform is of low computation complexity.

The color in the shade tabs is not completely uniform because of variations due to the surface texture, the crystalline nature of the ceramic, and to inhomogeneities in the firing process. For this reason, the shade guide colors are sampled from a rectangular region, and not from a single point location. Having a large sample of the color values allows the variation in color of each of the tabs in the shade guide to be statistically quantified.

Once the shade table has been constructed, every pixel measured by the CCD camera can be compared to colors of the shade guide. A weighted mean is done of the pixel value and of the values of the surrounding pixels. The central pixel is then classified as the color of the shade guide having the closest color to the mean.

The main difficulty of measuring translucency and color simultaneously arises from the fact that the information of these two appearance factors is usually confounded. Different approaches can be used to disambiguate these two appearance factors:

The auto-correlation functions for the three color channels provide information on the blur which can be caused by the translucency. Structured lighting can be used to increase and further disambiguate the signal.

Translucency can be evidenced by comparing successive images taken with alternately a white and a black background. A structured background can also be used to evidence transparency.

The knowledge of the color space covered by the material can also be used to parse color and translucency variations.

For the present application, the latter approach is possible because of the surprising two-fold observation that:

a. With increasing translucency, intensity decreases and the hue shifts toward blue; and
b. While for typical tooth shade variations, an intensity decrease corresponds to hue shifting toward the red (higher a*-value).

A translucency index is therefore determined with respect to a reference point (the most opaque region) by the product of the relative intensity variation with the red/blue relative difference. A logarithmic scale provides a perceptually more significant measure.

The reference point is the most opaque region of the tooth. It is obtained by an iterative procedure starting at a naturally opaque region determined by knowledge of the morphology of the tooth.

At every point, the translucency value is based on the median over a small neighborhood of points to eliminate biases due to outliers. A translucency image map may thus be built.

In the L*a*b*-color space show that for natural tooth shades L* to vary between 55 and 85, a* between 4.0 and 10.0, and b* between 16.0 and 28.0. We can divide the shade range in 5 groups with equidistant levels of lightness L*, as shown in table 1:

TABLE 1

| Shade group | Sub group | Opacious dentin | | | Dentin | | | Incisal | | |
|---|---|---|---|---|---|---|---|---|---|---|
| | | L* | a* | b* | L* | a* | b* | L* | a* | B* |
| 1 | 1 | 85.0 | 4.0 | 16.0 | 80.0 | 4.0 | 16.0 | 75.0 | 4.0 | 16.0 |
| | 2 | 85.0 | 5.0 | 20.0 | 80.0 | 5.0 | 20.0 | | | |
| 2a | 1 | 80.0 | 4.0 | 17.0 | 75.0 | 4.0 | 17.0 | 70.0 | 4.0 | 17.0 |
| | 2 | 80.0 | 6.0 | 25.5 | 75.0 | 6.0 | 25.5 | | | |
| 2b | 1 | 80.0 | 4.5 | 15.0 | 75.0 | 4.5 | 15.0 | | | |
| | 2 | 80.0 | 8.0 | 22.0 | 75.0 | 8.0 | 22.0 | | | |
| 3a | 1 | 75.0 | 5.0 | 17.5 | 70.0 | 5.0 | 17.5 | 65.0 | 5.0 | 17.5 |
| | 2 | 75.0 | 8.0 | 28.0 | 70.0 | 8.0 | 28.0 | | | |
| 3b | 1 | 75.0 | 6.0 | 15.0 | 70.0 | 6.0 | 15.0 | | | |
| | 2 | 75.0 | 9.0 | 22.5 | 70.0 | 9.0 | 22.5 | | | |
| 4a | 1 | 70.0 | 5.0 | 17.5 | 65.0 | 5.0 | 17.5 | 60.0 | 5.0 | 17.5 |
| | 2 | 70.0 | 8.0 | 28.0 | 65.0 | 8.0 | 28.0 | | | |
| 4b | 1 | 70.0 | 6.0 | 15.0 | 65.0 | 6.0 | 15.0 | | | |
| | 2 | 70.0 | 9.0 | 22.5 | 65.0 | 9.0 | 22.5 | | | |
| 5 | 1 | 65.0 | 6.0 | 15.0 | 60.0 | 6.0 | 15.0 | 55.0 | 6.0 | 15.0 |
| | 2 | 65.0 | 10.0 | 25.0 | 60.0 | 10.0 | 25.0 | | | |

As most oral color scanners have a suggestion which color or which mixture of two colors have to be used to approximate the color measured, the present invention will approximate the color by using a layering of two (or more) layers. Because the translucency of dentin porcelain, a layer with a different shade will effect the color experienced from the outside, stronger when the distance to the surface is less, as shown in FIG. 6.

| $h_1$ = 0.0 mm | $h_1$ = 0.2 mm | $h_1$ = 0.4 mm | $h_1$ = 0.6 mm |
|---|---|---|---|
| L* = 80.0 | L* = 78.42 | L* = 76.67 | L* = 75.0 |
| a* = 6.0 | a* = 6.0 | a* = 6.0 | a* = 6.0 |
| b* = 25.5 | b* = 25.5 | b* = 25.5 | b* = 25.5 |

To calculate the color of the layered porcelain the method of linear additivity of the color L*a*b* CIELAB units was used.

Several methods for producing near-net shaping restorations have led to a number of techniques known as solid freeform fabrication (SFFSuch techniques use computer-controlled robotics. One of the advantages of SFF over grinding and milling (example 1) include lower tooling costs.). Solid freeforming is the creation of a shape by point, line or planar addition of material without confining surfaces other than a base. This base can be a refractory ground block or a flat plate. It allows restorations designed with the computer software to be created without the use of molds or specific tooling using a wide range of building methods. The 3D computer images generated with CAD software is sliced to produce 2D images and then used to control a fabrication unit which manufactures the restoration layer by layer. To date, several SFF techniques, including stereolithography (SLA), selective laser sintering, fused deposition of ceramics (FDC), laminated object manufacturing (LOM), three dimensional printing (3DP) and robocasting. These last two are used in example 2 and 3 respectively. In stereolithography a photocurable ceramic suspension is used. Selected areas of each layer of the suspension is cured by UV light as the restoration is fabricated. Fused deposition of ceramics uses ceramic-binder formulations which are extruded into filaments. The hardware used is a heated nozzle (250–640 μm diameter) maintained at 100–150° C., which extrudes the fused filament according to a computer controlled pattern, initially depositing material at the perimeter of the restoration, then inside, repeating layer by layer. Selective laser sintering uses $CO_2$ laser beam to densify selected areas of ceramic powder deposited in thin layers. In laminated object manufacturing, laser cut layers of foil are stacked to produce the shape. Recently modified versions of LOM have been used in the forming of ceramics. Individual slices of tape cast ceramics were cut from the tape and stacked to assemble the computer-aided design.

EXAMPLE 1

A method for determining the color of an object by decomposing the light with an optical system consisting of achromatic doublets and by analyzing the light by means of interference filters and photo detectors, e.g. a device for decomposing the light such as a spectrophotometer.

As most oral color scanners have a suggestion which color or which mixture of two colors have to be used to approximate the color measured, the present invention will approximate the color by using a layering of two (or more) layers e.g. an opaque dentine with thereon a dentine porcelain layer. Because the translucency of dentin porcelain, a layer with a different shade will effect the color experienced from the outside, stronger when the distance to the surface is less, as shown in FIG. 6.

Integrating spheres are a known technique to achieve a uniform diffuse light source. This type of illumination is useful for measurement of matte surfaces. A drawback of that technique, or of any other technique that produces diffuse light, is apparent when it is used to illuminate glossy material. The desired signal is then confounded with a specular reflection component. The classification of tooth shades requires that the illumination be known with a precision of at least one percent everywhere on the tooth surface.

| Disk number | Total thickness C, mm | Thickness $h_1$ OD, mm | Thickness $h_2$ D, mm |
|---|---|---|---|
| 1 | 0.50 | 0.50 | 0.00 |
| 2 | 0.50 | 0.375 | 0.125 |
| 3 | 0.50 | 0.25 | 0.25 |
| 4 | 0.50 | 0.125 | 0.375 |
| 5 | 0.50 | 0.00 | 0.5 |
| 6 | 1.00 | 1.00 | 0.00 |

-continued

| Disk number | Total thickness C, mm | Thickness $h_1$ OD, mm | Thickness $h_2$ D, mm |
|---|---|---|---|
| 7 | 1.00 | 0.75 | 0.25 |
| 8 | 1.00 | 0.50 | 0.50 |
| 9 | 1.00 | 0.25 | 0.25 |
| 10 | 1.00 | 0.00 | 1.00 |

A total of 10 disks were fabricated according to table 2. Reflectance measurements R of the samples were made with a spectrophotometer with integrating sphere.

The $L^*, a^*$ and $b^*$ parameters were predicted and evaluated separately e.g. $L_{layer}^* = C_1 x h_1 x L_1^* + \ldots + C_i x h_i x L_i$ were $L_1^*$ is the predicted $L^*$ from the linear regression and $C_1$ is the concentration factor of pure shade 1 of layer 1 of thickness $h_1$.

In most of the present existing CAD/CAM-systems restorations are produced from massive material blocks in the dental laboratory or in the dental practice. Machining a restoration from a uniformly colored monolytic block of material can never fulfill both the esthetic demands and the requirements for strength. However, in the system according to the present invention crowns are produced via a sinter- and mill-process with a layered life-like ceramic, strengthened with a machined high-strength ceramic core. This way it is possible to improve the natural esthetics and strength obtained in free hand production of ceramic restorations.

The different steps are presented in the following sequence:
1. Optical scanning in the mouth of patient
2. Optical scanning of gypsum model
3. Design of restoration
4. Identify shade areas
5. Transfer in layers
6. Design of crown layer build-up
7. Production process The layering of the crown requires a series of ingenious production steps. To allow the subsequent sintering and milling steps, the refractory support, in which a negative of the interior of the restoration is ground first, should have the possibility to be reproducibly repositioned in the milling machine with high precision. This was solved with a double prismatic bottom part of the refractory block.

EXAMPLE 1

The tooth selected for measurement is brushed for one minute by the subject with tooth paste and tooth brush. The surface is wiped with a clean paper for saliva and moisture before measurement. Immediately after the cleaning procedure, the color of the tooth is measured by a spectroradiometric color computer. A white porcelain standard (X=95.720,Y=100.019,Z=92.159) of barium sulfate is used for calibration of the instrument.

Superimpose the mapped contour of the mirror tooth 4 onto the contour of the CAD designed computer crown contour 3 in FIG. 1. Superimpose the three areas 5, 6 and 7 in FIG. 3 found by the shade mapping onto the 2D-image of the newly designed tooth. Adjust $h_3$ according to the mapping of area 5 onto the designed crown. Identify area 5, 6 and 7 in FIG. 3 according to their respective lightness values.

The shade mapping analyzer is used to identify three different areas superimposed on the contour of the mirror tooth (FIG. 1). Area 6 (FIG. 3) is called the main tooth shade. From this tooth shade an appropriate color for the base layer 9 is selected.

The measured values in the three areas of the tooth for this example are as follows:

TABLE 3

| Area | $L^*$ | $a^*$ | $b^*$ | Identification |
|---|---|---|---|---|
| 5 | 79.6 | 5.4 | 25.1 | Opacious dentin |
| 6 | 74.6 | 5.3 | 22.9 | Dentin |
| 7 | 74.1 | 3.9 | 15.7 | Incisal |

The incisal shade area 7 (FIG. 3) closest lower lightness value match is shade group 1-1-incisal with $L^*=75.0$, $a=4.0$ and $b=16.0$.

The dentin shade of area 6 (FIG. 3) closest to the higher lightness value match is group 2A-2-dentin with $L^*=75.0$, $a=6.0$ and $b=25.5$. Table 4 shows the calculation of $h_2$.

TABLE 4

| Area 6 | L | a | b |
|---|---|---|---|
| Measured | 74.6 | 5.3 | 22.9 |
| Incisal, measured | 74.1 | 3.9 | 15.7 |
| Dentin, group 2A-2 | 75.0 | 6.0 | 25.5 |
| $h_{2,calculated}$, mm | 0.22 | 0.26 | 0.18 |
| $h_{2,average}$, mm |  | 0.22 |  |

The opacious dentin shade of area 7 with the closest higher lightness match is group 2A-2. The average h1-value to be used is 0.20 mm.

TABLE 5

| Area III | L | a | b |
|---|---|---|---|
| Measured | 79.6 | 5.4 | 25.1 |
| Dentin, measured | 74.6 | 5.3 | 22.9 |
| Opacious dentin, group 2A-2 | 80.0 | 6.0 | 25.5 |
| $h_{1,calculated}$, mm | 0.12 | 0.32 | 0.20 |
| $h_{1,average}$, mm |  | 0.20 |  |

An impression is made of the arch with the prepared teeth and poured in gypsum. The gypsum cast of the model that contains the preparation is marked with black/white contrast for unambiguous scanning of the margin.

The next step in the automated fabrication of a metal-ceramic crown is an optical impression obtained by laser scanning of the cast. The CAD/CAM system makes use of a fast laser-stripe scanning method to measure the 3D geometry of the preparation and its immediate surroundings and the opposing teeth. A straight laser stripe, which is projected onto the cast, is deformed by the 3D occlusal geometry of the tissues, and this deformation is used by the computer to determine the actual 3D positions of those points on the surface of the tissues. A charged coupled device (CCD) camera scans the projected line. The model is placed in the scanner clamping device, see FIG. 5, so that the path of insertion coincides approximately with the vertical z-axis of the scanner.

A rough overall-scan, using steps between consecutive scan lines of 0.2 mm, of the total arch with the preparation is made and converted to a gray-scale Z-chart. In this relief map of the scan, the location of the preparation, the approximal contacts and the extent of the scan area and the neighboring elements are entered. The incisal point, and a cusptip on the last molar bilaterally are marked by clicking on the screen using the mouse. From this information the orientation of the occlusal plane in the masticatory system is defined and the scanner software generates a scanning protocol that prevents shadowed parts.

Then, the antagonist impression on the model is fine-scanned, using steps between consecutive scan lines of 0.05 mm, with a high definition. After removal from the cast, the cast with the preparation is subsequently scanned. A computer generated surface of the prepared tooth is extracted from scan data. The accuracy of the scanning method lies preferably within 0.01 mm.

The design of a crown form follows the following procedural steps: selection of proper element from the library, modelling the crown on the screen to fit in with the remaining dentition and final adjustment of approximal contacts by the computer. A maxillary second pre-molar was designed on a die with a chamfer margin preparation. The appropriate tooth is chosen by the operator from an extensive collection of generic forms of theoretical teeth in the program's library. When an intact mirror-element can be found in the arch, it can be scanned and used as a standard tooth. The distal and mesial contacts indicated by the operator in the occlusal and buccolingual views of the scan form the first step in the fitting of the generic tooth. The margin line of the new crown is adjusted to the preparation line that was isolated automatically from the scan of the die.

The lingual and buccal boundaries are clicked in and dragged with the mouse, to shape the tooth so that it fits in a natural appearing row with the adjacent teeth. A warping algorithm generates a deformation field and deformation vectors within the field to generate the new form as directed by the drag vector indicated with the mouse. This way the external contours of the new crown can be adjusted interactively with the mouse, in much the same way of the building-up of porcelain by brush or spatula. After the crown has been fitted into the row, the computer adjusts the mesial and distal contacts to within +/−0.02 mm of the adjacent teeth.

The centric tooth-to-tooth contacts are obtained in relation to the quality of the opposing occlusal surface. Resulting contacts vary from a complex tri-podic occlusal situation in case of an ideal antagonist surface to a simple central contact on a less-defined occlusal surface.

The new crown is then superimposed on the opposing teeth which are displayed on the screen as a relief map. The CAD program deforms the generic tooth parametrically (with conservation of shape) according to gnathologic principles. On the library tooth preferred points of contact are used as anchor points to direct the search for contacts with the antagonist. The different fields of contacts of the crown are deformed to give maximal tooth-to-tooth contact with the opposing teeth. Because the theoretical tooth is brought into contact with antagonist as scanned, it can be assumed that contacts are also in the same range as the scanning accuracy, that is 0.01 mm.

The occlusal surface should allow cusps to escape and return to their fossae without interferences. Proper prosthetic fabrication should ensure that functional contact relationships are restored for both dynamic and static conditions. Maxillary and mandibular teeth should contact in a harmonious manner that allows optimum function, minimum trauma to the supporting structures, and an even distribution of load throughout the dentition. Positional stability of the teeth is critical if arch integrity and proper function are to be maintained over time.

After the interior and exterior tooth surfaces have been designed, several interface surfaces between cement and ceramic core and between dentine and incisal porcelain are defined. The software calculates the interior surface, corrected with marginal gap (0.03 mm), overall cement thickness (0.05–0.10 mm) and ceramic core-die cement thickness (0.02 mm) as specified by the operator. The cement gap geometry of the crown ensures that the cement thickness between the ceramic core and the die at a distance of 2 mm from the margin is defined smaller than the marginal cement gap. This way a better support from the ceramic on the inside, forming a step-up that will take most of the load exerted on the crown during placement and during mastication. The stress on the porcelain shoulder will be relieved because the high-alumina core substructure is closest to the die. A thickness of the ceramic core of 0.7–0.8 mm is used. A mapping of the calculated thickness of the restoration indicates to the operator possible thin spots that might need interactive correction of the designed layer build-up or external contours.

Through a controlled model of the layering incisal and body porcelain esthetic effects, such as natural translucency and opalescence, can be obtained. The high-strength alumina core has been shaded to give a back-ground tone for the more translucent ceramic layers.

The restoration is milled using standard diamond grinding tools. The exactly measured dimensions of each of the individual tools are entered into a dialog window of the Miller software on the screen through the key board.

The following cutting tools are used: a diamond cylinder grinder of 5.3 mm diameter, a diamond rounded disk grinder of 9.3 mm diameter, a diamond pointed tool of 0.9 mm. The tools are automatically exchanged as they are used and reset against a zero-switch.

Factory-standardized, preformed refractory blocks for single elements, which have a precision fit in the milling machine clamping device, are made of a soft machinable refractory material and are cylindrical with a diameter large enough to contain the maximum mesiodistal tooth diameter. The expansion of the refractory is balanced by varying the ratio of the constituting oxides such as silica, magnesia or alumina.

The refractory block is fixed in a high-precision vice in the milling machine and the negative of the inside surface of the crown is accurately milled using a cylindrical disc bur and a round carbide bur.

In the next processing step, a cylinder-shape of a high-strength ceramic of the appropriate color shade (C shade) is pressed by means of a dry bag isostatic pressing technique over the milled inside on the refractory block and presintered under vacuum. A pre-determined quantity of ceramic fills the rubber mold with the ground refractory block in the Center. The mold is placed inside a membrane that is put under hydraulic pressure. After it is sintered, the ceramic can be easily ground to a calculated oversize that takes account of the shrinkage that will occur during the final sintering. The final thickness of the high-strength ceramic is 0.6 mm. Then a dentinal porcelain paste in the appropriate shade area 6-shade (FIG. 3) is applied. From a capsule the porcelain is cold-pressed on the sintered alumiumoxide based ceramic layer on the refractory shape and fired under standardized conditions under vacuum. After firing of the porcelain, the refractory block is placed back into the precision vice of the milling machine and the interface between dentinal and incisal porcelain is milled. Then a second layer of dentin porcelain in shade area 6 is applied in the same way.

Then translucent incisal porcelain in the appropriate shade of area 7 (FIG. 3) is cold-pressed over the milled dentinal porcelain and fired, and the external surface of the crown is milled.

The last phase is a self-glazing step by heating to a temperature that lies 30 degrees under that of the incisal layer. A quick elevation to this temperature softens only the superficial layer and, therefore, enables creation of a superiorly glazed surface that reproduces the fine details without causing slumping. At the same time, the surface integrity that might have suffered from the grinding operation will be restored during this final glazing step. Polishing of the final restoration is not necessary because the glazing step is performed as a final treatment before the refractory is removed by grinding and air abrasion in the usual manner.

EXAMPLE 2

The restoration was designed as described in example 1.

One of the methods is 3D ink jet printing. In 3D jet printing a binder solution is used to fix the ceramic powder. First the design according to the present invention is converted into STL-files, which slices the designed restoration in hundreds or more of two-dimensional cross-sections (FIGS. 2 & 4 for example). The procedure is as follows:

1. The printing machine spreads a layer of powder of dental material from the source piston to cover the surface of the build piston. A platen reversing relay avowed indefinite overprinting. The time delay between printing adjacent layers was controlled The resolution of the printer was 200×216 dpi. A modified version of the BIO.DOT microdoser (BIO.DOT Ltd., Huntington, Cambridshire, UK) was used for continuous ink jet printing. It has three main sections:
   i. the ink control unit which contains ink jet printing and pressurizes ceramic ink using gas so that it flows, filters and recirculates
   ii. the unit that creates, directs and prints droplets of ink, and
   iii. the sliding table fitted with an optical track providing registration for automatic multi-layered printing The ceramic ink is pumped to the nozzle of 60 μm diameter under a pressure of about 400 kPa through an in-line filter which contains a series of metal and polymeric filters of decreasing aperture. The stream formed at the nozzle was broken-up into small droplets by the pressure wave created by the piezoelectric drive rod at a frequency of 64 kHz. The droplets were charged simultaneously by the charging electrode having a voltage between 50–285 V. A detector in the charging electrode determined whether effective charging of droplets was achieved. Droplets with correct charge were deflected by the 18 kV high voltage plates. The uncharged droplets were not deflected but collected through the return tube placed directly below the main jet and pumped back into the reservoir. The droplets were visible through a window at the printhead with the aid of LED illumination. The shape of the droplets were changed by controlling the modulation voltage.

The ink was dispersed using 2 wt % of Hypermer KD1 (ICI Surfactants, Midlesborough, UK). The presence of 2 wt. % ammoniumnitrate in a binary butylacetate-ethanol solvent mixture is used to produce a conductive ink. Polyvinylbutyral and dibutyl sebacate serve as the binder and plasticizer, respectively.

2. The machine then prints binder solution containing concentrated pigments or colloidal size ceramic onto the loose powder, forming the first cross-section. The binder solution is passed through the printer nozzle which scanned each layer of ceramic particles formed into shape by roll compaction. The ceramic particles are dispersed and stabilized in inks and undispersed agglomerates can either be removed by sedimentation or be filtered out on-line just prior to printing, allowing a high density to be obtained in subsequent sintering. Ink composition can be changed at each print point allowing components with varied composition and microstructure to be produced with excellent resolution. Where the binder is printed, the powder is glued together and at the same way a 2D color print of pigment deposited. The remaining powder remains loose and supports the layers that will be printed above. It is also possible to used a laser printer and laser-sinter the powder together.

3. When the cross-section is complete, the build piston is lowered slightly, a new layer of powder is spread over its surface and the process is repeated.

4. The dental restoration grows layer by layer in the build piston until the part is completely surrounded and covered by loose powder.

5. Finally, the build piston is raised and the loose powder is vacuumed away, revealing the completed part. This system is able to achieve an unrivaled build speed because the powder, which comprises the majority of the volume of he final restoration, is laid down quickly in bulk. The restoration has to be polished. After polishing the restoration has a natural appearance and the color that was designed.

EXAMPLE 3

Another method is the robocasting. This is a slurry depositing technique capable of producing near-net-shaped restorations that utilizes feedstocks of negligible organic binder content (<1 vol %). The restoration was designed according to the present invention as described in example 1. In robocasting pseudoplastic suspensions (solids volume fraction ca. 0.50 are deposited onto a substrate, such as described in the first example: a ground refractory block (example 1), in a precise pattern, according to an 2D surface (FIG. 2) On minimal drying, the as-deposited suspension undergoes a liquid-to-solid transition that freezes-in the structure of the patterned restoration. The suspension is deposited in a precise pattern onto a moving X-Y table via computer aided design (CAD) instruction. The 3D restoration is constructed using a layer-by-layer build sequence (FIG. 5). First the CAD-design of the restoration is converted into STL-files, which slices the designed restoration in hundreds or more of two-dimensional cross-sections (FIG. 2 & $ for example).

A porcelain powder (Sintagon, Elephant Dental B.V.) was micronised for 4 hours in a vibratory ball mill. Darvan C (R.T. Vanderbilt Co), a 25% aqueous solution of ammonium polymethacrylate (APMA), was used as a dispersant in a quantity of 1.2 wt % of the porcelain. Partially hydrolysed PVA (405S, Kuraray International Corp., Tokyo, Japan), with a degree of hydrolysis of 80.8 mol % and an average molecular weight of 28700 g/mol, was added. Tyzor TE (DuPont Chemicals, Deepwater, N.J.) was used as a crosslinking agent, because it reacts with PVA to form a gel. Tyzor TE contains 8.3 wt % titanium, and consists of a 25 wt % solution (in isopropylalcohol) of various organotitanate chelates. The pH was adjusted to 8.5 using $HNO_3$ or $NH_4OH$. The suspension was defoamed by addition of 0.25% 1-octanol by volume of solution and mixed for 2 h using a slow roll mill before casting. The cross-linking agent concentration was 0.0063 g of titanium/ml solution. The porcelain suspension and the cross-linking agent (Tyzor TE) solution were loaded into separate 30 ml polyethylene syringes. The system consists of a two-nozzle delivery system. The syringes were clamped to the SFF apparatus (CAMM3, Roland, Tokyo, Japan), each of which was fitted with a cooling coil that chilled the gelcasting components to 15° C. to minimize chelation in the mixing chamber. The porcelain suspension and the cross-linking agent were pumped into the mixing chamber at a controlled ratio, homogenized using a paddle type mixer, extruded from the tip orifice, and deposited in a precise pattern onto The refractory ground block on a moving X-Y table. Three-dimensional build-up was realized by step wise increasing the Z-axis using a layer-by-layer build sequence. The X-Y-table, and thus the refractory block was heated to 30° C. to enhance gelation kinetics in the deposited layers. The restoration was dried in air and sintered at 900° C. for 5 minutes under vacuum. The resulting restoration has a very natural appearance with colors as designed.

This invention is not only concerned with ceramics the same methods can be used with acrylic composite materials.

Although the present invention was described above in detail, it is to be noted here, that the description only refers to specific embodiments and that the scope of the present invention is only and exclusively defined by the accompanying claims. For instance, specific materials are mentioned, but the invention is not limited thereto and acrylic materials can be used in stead of ceramic or porcelain materials. Other methods to construct the layered configuration of an artificial tooth than those, which have been explicitly described, can also be considered. Examples thereof are stereolithography, fused deposition, etc. Any and all such additions and alternatives within the scope of the accompanying claims are well within the reach of the skilled person. Further a method according to the present invention can be such that a build-up of multiple layers, even in the form of a continuous series, is used, or that multiple areas over the outer surface of the artificial tooth in correspondence with the natural or corresponding tooth, even in the form of one or more pixels, are defined and reproduced.

The invention claimed is:

1. A method for producing an artificial tooth, comprising a base layer substantially determining strength and at least one cover layer substantially determining appearance of a finished artificial tooth, said method comprising:

establishing the available outer shape and dimensions for the finished artificial tooth;

acquiring an image of: (i) a natural tooth to be replaced by the artificial tooth; or (ii) a corresponding natural tooth, the image acquired over at least the in-use visible outer surface thereof, including variations in appearance in said outer surface;

determining variations in the appearance determining properties of the cover layer to correspond with the variations in the appearance of the natural tooth to be replaced or the corresponding natural tooth, and determining a thickness of the cover layer locally required for said correspondence;

constructing the base layer to a shape and dimensions, which are based on the shape and dimensions available for the artificial tooth and, prior to construction, deducting therefrom the locally required thickness of the cover layer; and applying the cover layer over the base layer to attain the available outer shape and dimensions for the finished artificial tooth.

2. The method according to claim 1, further comprising the step of applying an additional cover layer within the same dimensional limitations, the cover layer and the additional cover layer having different appearance determining properties and together determining the appearance of the finished tooth.

3. The method according to claim 2, wherein varying the appearance determining properties comprises varying the thicknesses of the cover layer and the additional cover layer.

4. The method according to claim 3, further comprising the steps of:

adjusting at least one of the shape, thickness, form and dimensions of the base layer, further taking into account the minimum thickness of the base layer as well as the thickness of the cover layer or layers, and constructing the base layer to the adjusted specifications before applying the cover layer.

5. The method according to claim 4, further comprising the step of: forming at least one of the base layer and the cover layer with at least one of 3D ink jet printing using STL files, robocasting of material, stereolithography (SLA), fused deposition (FD), and laminated object manufacturing.

6. The method according to claim 3, further comprising the step of: forming at least one of the base layer and the cover layer with at least one of 3D ink jet printing using STL files, robocasting of material, stereolithography (SLA), fused deposition (FD), and laminated object manufacturing.

7. The method according to claim 2, further comprising the step of: forming at least one of the base layer and the cover layer with at least one of 3D ink jet printing using STL files, robocasting of material, stereolithography (SLA), fused deposition (FD), and laminated object manufacturing.

8. The method according to claim 1, wherein varying the appearance determining properties comprises varying the thickness of the cover layer.

9. The method according to claim 8, further comprising the steps of: adjusting at least one of the shape, thickness, form and dimensions of the base layer, further taking into account the minimum thickness of the base layer as well as the thickness of the cover layer or layers, and constructing the base layer to the adjusted specifications before applying the cover layer.

10. The method according to claim 8, further comprising the step of: forming at least one of the base layer and the cover layer with at least one of 3D ink jet printing using STL files, robocasting of material, stereolithography (SLA), fused deposition (FD), and laminated object manufacturing.

11. The method according to claim 1, where varying the appearance determining properties comprises varying the physical material properties of at least the cover layer.

12. The method according to claim 11, further comprising the step of locally adding an additive to the material for at least the cover layer.

13. The method according to claim 11, further comprising the step of: forming at least one of the base layer and the cover layer with at least one of 3D ink jet printing using STL files, robocasting of material, stereolithography (SLA), fused deposition (FD), and laminated object manufacturing.

14. The method according to claim 1, further comprising the step of: forming at least one of the base layer and the cover layer with at least one of 3D ink jet printing using STL flies, robocasting of material, stereolithography (SLA), fused deposition (FD), and laminated object manufacturing.

15. The method according to claim 1, where a build-up of a plurality of layers is used.

16. The method of claim 15, wherein the plurality of layers are in the form of a continuous series.

17. The method according to claim 1, where a plurality of areas over the outer surface of the artificial tooth in correspondence with the one of the natural and corresponding tooth are defined and reproduced.

18. The method of claim 17, wherein the plurality of areas are in the form of at least one pixel.

19. The method of claim 1, wherein at least one of the establishing step and the deducting step is performed by a CAD-CAM system.

20. The method of claim 1, further comprising the step of forming at least one of the base layer and the cover layer with robocasting of material, wherein the material robocasted is in gel form.

* * * * *